United States Patent
Tylke

(10) Patent No.: US 9,364,631 B2
(45) Date of Patent: Jun. 14, 2016

(54) INTUBATING FORCEPS AND ASSOCIATED METHOD

(71) Applicant: James Tylke, Jupiter, FL (US)

(72) Inventor: James Tylke, Jupiter, FL (US)

( * ) Notice: Subject to any disclaimer, the term of this patent is extended or adjusted under 35 U.S.C. 154(b) by 139 days.

(21) Appl. No.: 14/080,088

(22) Filed: Nov. 14, 2013

(65) Prior Publication Data

US 2014/0135787 A1    May 15, 2014

Related U.S. Application Data

(60) Provisional application No. 61/726,424, filed on Nov. 14, 2012.

(51) Int. Cl.
 *A61F 11/00* (2006.01)
 *A61M 16/04* (2006.01)
 *A61B 17/28* (2006.01)

(52) U.S. Cl.
 CPC ............ *A61M 16/0488* (2013.01); *A61B 17/28* (2013.01)

(58) Field of Classification Search
 CPC . A61M 16/0488; A61B 17/28; A61B 17/282; A61B 2017/2945; A61B 17/00008; A61B 17/12; A61B 17/12009; A61B 17/12013; A61B 17/132; A61B 17/1322; A61B 17/1325; A61B 17/1327; A61B 17/267; A61B 17/2676; A61B 17/2812; A61B 17/29; A61B 2017/1125; A61B 2017/12004; A61B 2017/2808; A61B 2017/2901; A61B 2017/2904; A61B 2017/2926; A61B 2017/2927; A61F 6/20
 See application file for complete search history.

(56) References Cited

U.S. PATENT DOCUMENTS

| | | | |
|---|---|---|---|
| 6,319,257 B1 * | 11/2001 | Carignan | A61F 2/4601 606/205 |
| 7,438,717 B2 * | 10/2008 | Tylke | A61B 17/28 600/434 |

* cited by examiner

*Primary Examiner* — Jonathan W Miles
*Assistant Examiner* — Kankindi Rwego
(74) *Attorney, Agent, or Firm* — Kevin P. Crosby; GrayRobinson, P.A.

(57) ABSTRACT

Forceps having arms pivotally connected for relative movement between an opened position and a closed position include a tube guide formed by arcuate guide portions on each arm. The tube guide includes an inwardly facing arcuate inside wall surface sized for slidable engagement with a tube. The tube guide is fixed at a right angle to the arms and includes a gap formed between tip ends of each of the arcuate guide portions when the arms are in the closed position. Each arm includes a bend fixed at distal ends, wherein the bend is positioned at a distance from the tube guide to form a distal arm portion for each arm permitting an improved view during use of the forceps.

18 Claims, 12 Drawing Sheets

TABLE: FINISHED FORCEPS FEATURES

| ELEMENT | PEDIATRIC | ADOLESCENT | ADULT | COMMENTS |
|---|---|---|---|---|
| TIP OD | 8.0 mm | 12.5 mm | 15.0 mm | CLOSED |
| TIP ID (244) | 6.2 mm | 9.5 mm | 12.0 mm | CLOSED |
| TIP THICKNESS | 3.0 mm | 3.5 mm | 4.0 mm | DESIRABLE |
| TIP HEIGHT | 12.5 mm | 16.75 mm | 20.5 mm | DESIRABLE |
| GAP (230) | 3.0 mm | 4.5 mm | 6.0 mm | CLOSED |
| GAP/2πR | 13.6 % | 15.0 % | 15.9 % | RATIO |
| ARM LENGTH (242) | 20.0 mm | 30.0 mm | 40.0 mm | TO BEND AT DISTAL END |
| ARM THICKNESS | 1.5 mm | 2.0 mm | 3.0 mm | DESIRABLE |
| TIP BASE | 5.0 mm | 6.0 mm | 7.0 mm | CLOSED POSITION |
| TIP/ARM ANGLE | 90° | 90° | 90° | FIXED |
| ARM ANGLE (238) | 11.5° | 11.5° | 11.5° | FIXED |
| PREFERRED ENDOTRACHEAL TUBE OD (130) | 2.5 mm- 4.0 mm | 4.5 mm- 6.0 mm | 6.5 mm- 8.0 mm | RANGE |
| OTHER: RATIO TUBE/ID | 0.36-0.57 | 0.47-0.63 | 0.54-0.67 | RATIO |
| OTHER: RATIO GAP/TUBE | 1.2-0.75 | 1.0-0.75 | 0.92-0.75 | RATIO |
| OTHER: RATIO GAP/ID | 0.43 | 0.47 | 0.50 | RATIO |
| OTHER: TUBE - GAP (mm) | 0.25 | 0.75 | 1.25 | AVERAGE TUBE DIAM |
| OTHER: RATIO TUBE/GAP | 1.08 | 1.17 | 1.2 | AVERAGE TUBE DIAM |

FIG. 7

INTUBATING FORCEPS AND ASSOCIATED METHOD

FIELD OF THE INVENTION

The present invention relates generally to medical equipment. More particularly, the present invention relates to intubation aides, such as forceps, used to guide tubes during insertion into a patient's body.

BACKGROUND

As described in U.S. Pat. No. 7,438,717 to Tylke for an Anesthesia Intubating Forceps, the disclosure of which is herein incorporated by reference in its entirety, medical professionals have used various tools and implements in their treatment of patients that involve insertion of a catheter into a patient, including oral or nasal endotracheal intubation, during which the medical professional typically inserts a nasal or oral endotracheal tube into the trachea to assist with ventilation for the patient.

In order to assist with endotracheal intubation, an implement, such as forceps, is used by the medical professional to guide and/or direct the catheter/endotracheal tube into the proper place. A laryngoscope may also be used during nasal and oral endotracheal intubation to depress and secure the patient's tongue and lift the jaw to expose the vocal cords. When the patient's head is tilted back, as is done during the intubation procedure, and the tongue and jaw are lifted securely, the medical professional performing the intubation should have an unobstructed view of the patient's vocal cords, provided there are no foreign objects or fluids in the patient's mouth. However, when the medical professional inserts placing forceps into the patient's mouth, the view is severely obstructed by his or her hand and by the forceps themselves. Pre-existing forceps did not permit a clear view of the area of concern, nor allow the medical professional to grasp and control the tube adequately, making endotracheal intubation difficult and time-consuming, which could mean the difference between life and death for a patient that requires assistance with ventilation.

In endotracheal intubation situations, a key problem with many medical forceps is that the medical professional is required to grip or grab the nasally or orally-inserted catheter or tube in the back of the pharynx and try to place the tube through the patient's vocal cords by frequently gripping, releasing and re-gripping the lubricated catheter or tube, which is also coated with nasal and oral secretions and possibly blood in a traumatic situation. These forceps frequently have serrated edges or teeth, which used to assist in gripping antiquated rubber catheter tubes but also can snag, catch on or tear the soft tissues inside the patient's mouth and throat and damage the patient's vocal cords. Even if the patient is not harmed, these sharp edges on the forceps can rupture the insufflation balloon while attempting to grab the lower end of an endotracheal tube during a potentially difficult tube placement procedure, which must be inflated once the endotracheal tube is inserted past the patient's vocal cords to create an air-tight seal with the trachea and allow for positive pressure ventilation.

Tylke '717 identifies a need to provide catheter-guiding forceps that allow a medical professional to have easy access to difficult-to-reach areas of a patient's body, such as in an oral or nasal endotracheal intubation, while simultaneously allowing the medical professional to have an unobstructed or virtually unobstructed view of the area in the patient's body in which the medical professional is working, such as the patient's glottis or vocal cords. As a result, forceps were provided with a pair of scissor-like handles that are pivotally connected to each other and that continue past the pivot to form a pair of arms with at least two bends in the handles immediately before the pivot. As a result, the medical professional is allowed to place the distal, guiding end of the forceps in a desirable location within the pharynx while simultaneously permitting a desirable view of the area of concern, particularly, in the circumstance under discussion, the patient's vocal cords, because the medical professional's hand holding the forceps is not in a line of sight of the area through which the tube is to be placed while using the forceps. During endotracheal intubation, the medical professional places the forceps in registry with the patient's oropharynx (i.e., the back of the throat). Then, the catheter (e.g. endotracheal tube) can be guided through the forceps and past the patient's vocal cords through the glottis (i.e., the aperture through the vocal cords), where ventilation is optimized. As a result, the medical professional does not have to grip and re-grip the catheter tube during this process, saving critical time from passing in a potentially life-threatening circumstance, and eliminating the risk of harm to the patient vocal cords and adjacent tissue as well as the catheter or tube that re-gripping may cause.

While improvements to then known forceps were provided, including satisfying a need for forceps that allow a catheter tube to easily pass through the forceps tip instead of requiring frequent re-gripping of the slippery catheter tube, there continues to be a need to allow the medical professional to efficiently manipulate the endotracheal tube while minimizing the potential for harm to the patient.

SUMMARY

In view of the foregoing background, embodiments of the invention may comprise forceps having first and second arms pivotally connected by a pivot for relative movement between an opened position and a closed position, each arm having a distal end and a proximal end. A tube guide having an opening therethrough may be formed by first and second arcuate guide portions in combination when the arms are in or proximate the closed position. The tube guide may include an inwardly facing arcuate inside wall surface forming the opening, wherein the opening is sized for slidable engagement with a tube to permit free longitudinal movement therewith. In one embodiment, the first and second arcuate guide portions may be fixed substantially perpendicularly to the arms. The tube guide includes a gap formed between tip ends of each of the first and second arcuate guide portions when the arms are in the closed position. Each arm may optionally include a bend fixed at distal ends thereof, wherein the bend is positioned at a distance from the tube guide forming a distal arm portion for each arm with a length dimension at least three times a diameter of the opening.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 7 is a Table illustrating exemplary forceps dimensions for pediatric, adolescent and adult patients;

DETAILED DESCRIPTION OF EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notations are used to indicate similar elements in alternate embodiments.

Figure 1:
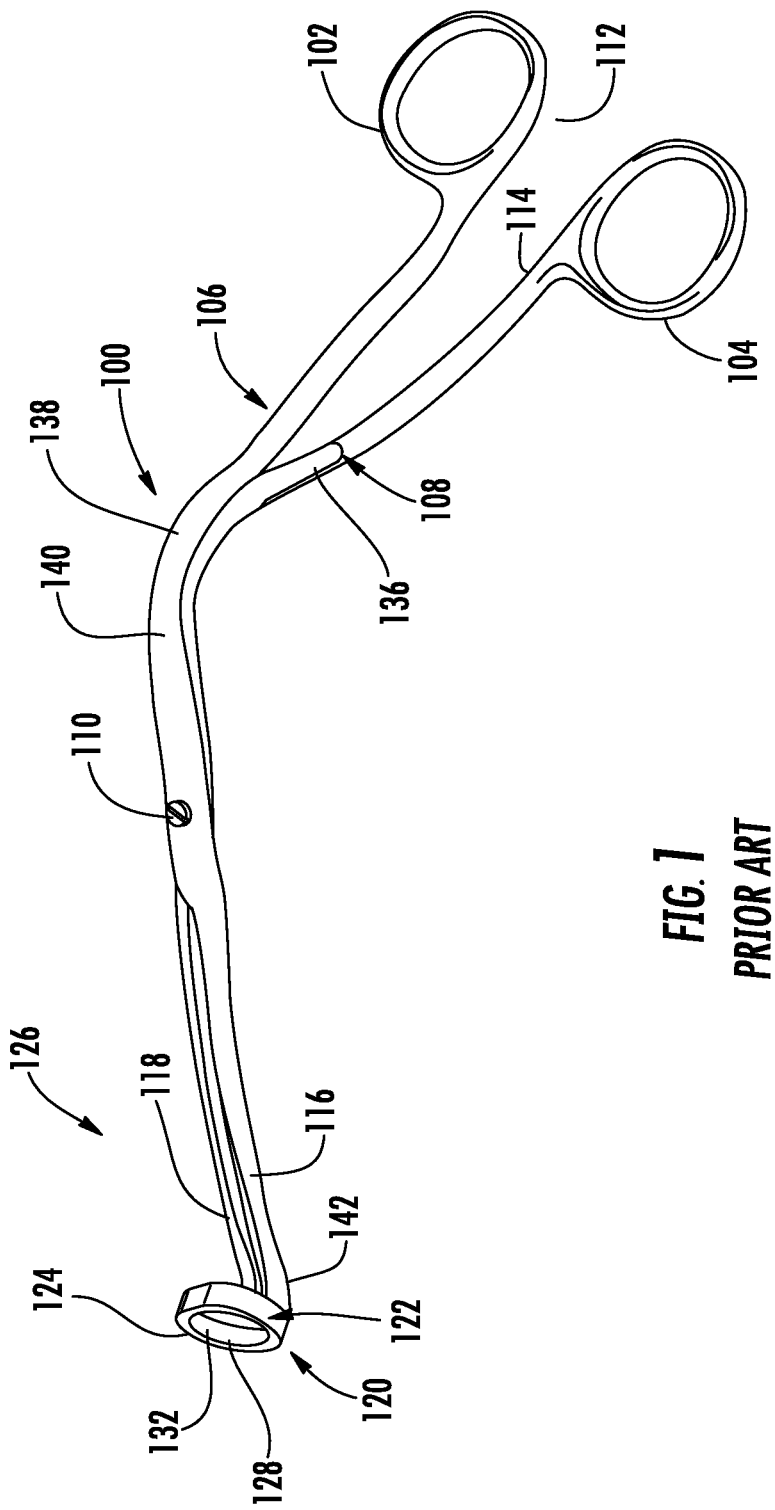
FIG. 1 is a perspective view of known forceps illustrated in a fully closed position.
Figure 2:
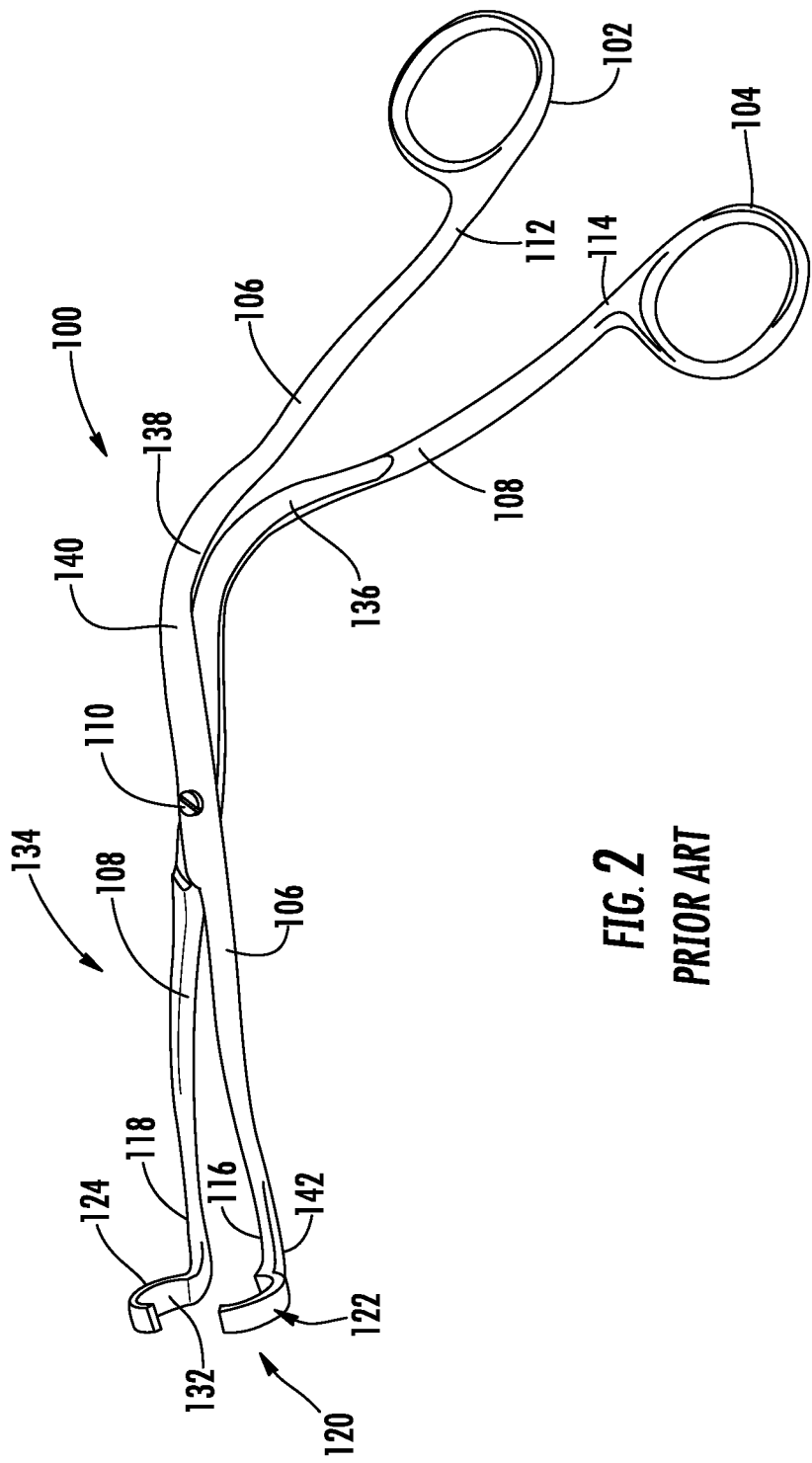
FIG. 2 is a perspective view of the known forceps of FIG. 1 illustrated in an open position.
Figure 3:
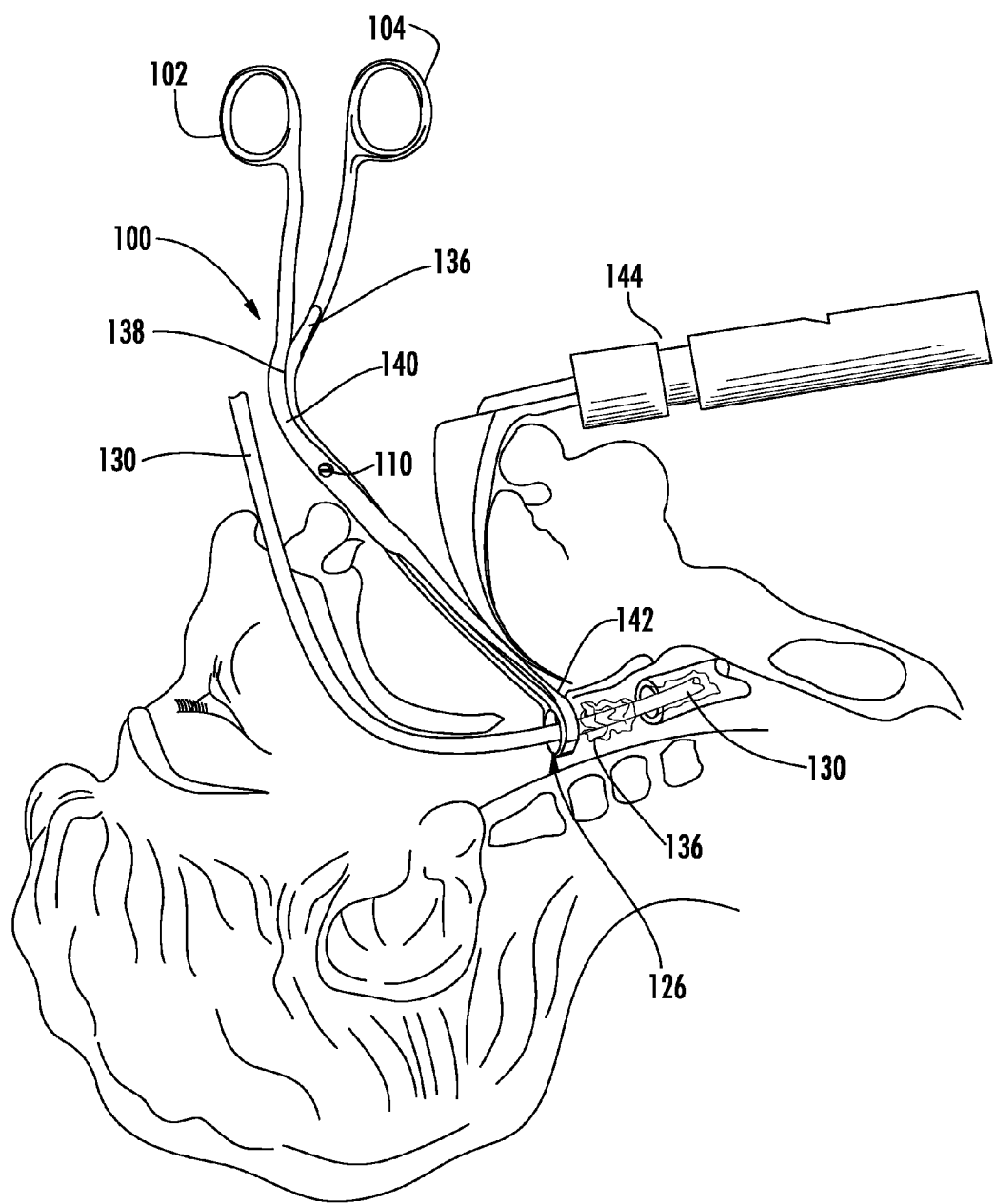
FIG. 3 is a diagrammatical illustration of a forceps and a laryngoscope used to insert an endotracheal tube into a patient.

With reference initially to FIGS. 1 and 2, one known forceps, as described in U.S. Pat. No. 7,438,717, is herein described as forceps 100 having a pair of handles 102, 104, each defining a gripping portion upon which the medical professional can place his or her fingers to operate the forceps. The handles 102, 104 are integrally connected to a pair of arms 106, 108. The arm 106 is pivotally connected to the arm 108 at a pivot 110. Each arm 106, 108 is herein described as having a proximal end 112, 114 and a distal end 116, 118, respectively. The handles 102, 104 are attached to the proximal ends 112, 114, respectively. A forceps tip 120 is formed by tip ends 122, 124 at distal ends 116, 118 of each arm 106, 108. Each tip end 122, 124 is substantially semicircular in shape. The shape of the ends 122, 124 may, within the scope of the invention, be any shape that would allow the ends to form a guide 128 when in a closed position 126, as illustrated with continued reference to FIG. 1, such that a catheter or endotracheal tube 130 may be easily passed therethrough. When the arms 106, 108 are in the closed position 126, the ends 122, 124 in combination form the guide 128 adapted to receive and guide the tube 130 so that the tube can be advanced through the patient's vocal cords, as illustrated with reference to FIG. 3.

In the closed position 126, the interior surface 132 of the guide 128 formed by the ends 122, 124 is slightly larger than the diameter of a standard-sized tube 130. It is desirable that the tube 130 be able to be slid within the guide 128 when the forceps is in the closed position 126.

With reference again to FIG. 3, the forceps 100, herein described by way of example, is typically used to insert the tube 130 into a patient, wherein a health care professional will insert his or her fingers into apertures of the handles 102, 104 and opens the handles, which correspondingly open distal ends 116, 118 of the arms 106, 108 for placing the forceps in an open position 134, as illustrated with reference again to FIG. 2 depicting the forceps 100 in the open position. The tube 130 is then passed between the tip ends 122, 124. The arms 106, 108 are positioned so that the guide 128 is placed in registry with the patient's glottis (the opening in the vocal cords) so that the tube 130 can be accurately inserted into the proper location in the patient's body, such as through the patient's vocal cords.

With reference again to FIGS. 1-3, the forceps 100 described in Tylke '717 comprises a first bend 136 and a second bend 138 that allow the medical professional to have an unobstructed view of the patient's vocal cords or other body part into which the catheter is to be inserted. This allows for faster and more accurate insertion of the tube 130, without risk of harm to the patient or damage to the tube that typically arises when the medical professional must grip and re-grip the catheter as with earlier known forceps. It was determined that the combination of the first and second bends 136, 138 provides an unobstructed view of the patient's vocal cords because the user's hand that holds the forceps 100 is offset to a side of the mouth while the guide 128 is in registry with the glottis. Further, Tylke '717 describes a third bend 140 that contributes to the unobstructed view of the patient's vocal cords. The three bends 136, 138, 140 are on the proximal end of the arms 106, 108 and on a handle side of the pivot 110. A fourth bend 142 is also described, located immediately before the tip 120 in each of the tip ends 122, 124. The fourth bend 142 is used to rotate the tip 120 approximately fifteen degrees clockwise from their otherwise standard position, although a greater or lesser magnitude of bend may be desirable as will occur to the person of skill in the art. The fourth bend 142 may be at an acute angle or may rotate the tip 120 in an opposite direction, creating an obtuse angle. The angle of insertion of the tube 130 through the guide 128 is changed by the fourth bend 142, allowing for an easier insertion in patients that have a shorter neck, such as children or small adults.

By way of example and with reference again to FIG. 3, one use of the forceps 100 with a laryngoscope 144 is illustrated in a patient for a nasal endotracheal intubation, wherein the tube 130, herein a ventilation tube, is inserted into the patient's nose and is passed through the patient's sinus cavity into the back of the patient's throat. As is well known, the laryngoscope 144 is used to secure the patient's tongue and provide light to the patient's airway. As the medical professional holds the forceps 100 in registry with the patient's glottis, a medical assistant, such as a nurse, will advance the ventilation tube 130 through the ends 122, 124 of the forceps 100 forming the guide 128 and through the patient's glottis. After being properly located, a balloon portion 146 of the tube 100 may be inflated to secure a seal and allow for proper ventilation.

After extensive experimentation and trials, further improvements to forceps have been discovered, and are herein described with reference to improvements to the Tylke '717 forceps 100 above described by way of example. However, it will be appreciated by those of ordinary skill in the art that the improvements presented below may be applied to forceps in general.

Figure 4:
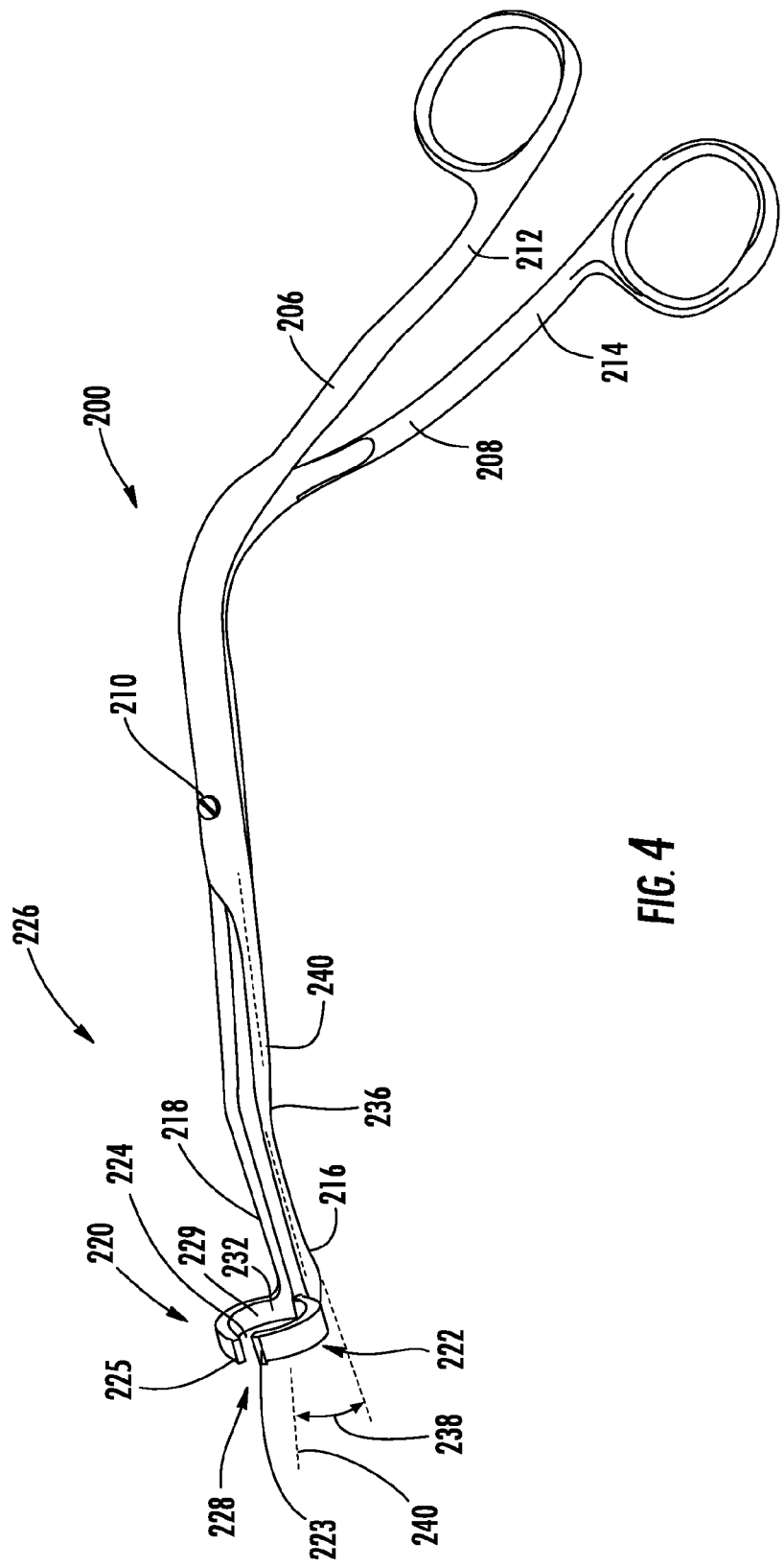
FIG. 4 is a first perspective view of one embodiment of forceps in keeping with the teachings of the present invention.

With reference to FIG. 4, improvements to the forceps 100 above described are illustrated with reference to forceps 200, wherein embodiments and teachings of the present invention resulting from testing and experimentation are now presented by way of example.

Figure 8:
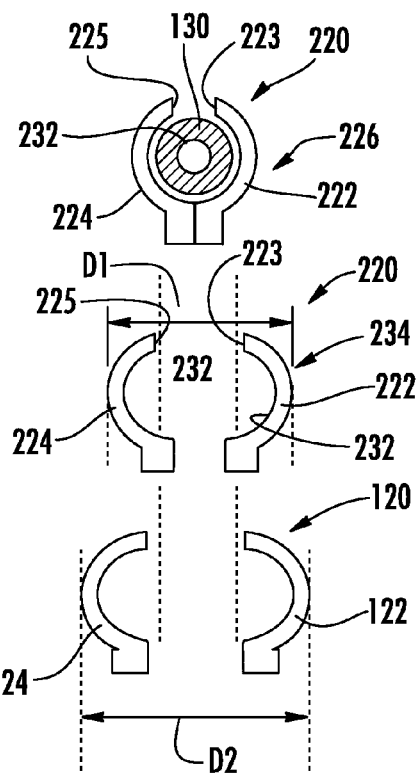
FIG. 8 is a diagrammatical illustration including partial end views of the embodiment of FIG. 5 in closed and open positions, and of a prior art forceps tip in an open position.

The forceps 200 are herein described as comprising first and second arms 206, 208 pivotally connected by a pivot 210 for relative movement between an opened position 234, illustrated and later discussed with reference to FIG. 8, and a closed position 226, wherein each arm 206, 208 is defined as having a distal end 216, 218 and a proximal end 212, 214. A tip 220 comprises a first arcuate guide portion 222 at the distal end 216 of the first arm 206 and a second arcuate guide portion 224 at the distal end 218 of the second arm 208. As a result, a tube guide 228 having an opening 229 therethrough is formed by the first and second arcuate guide portions 222, 224 in combination when the arms 206, 208 are in or proximate the closed position 226. The tube guide 228 includes an inwardly facing arcuate inside wall surface 232 forming the opening 229. The opening 229 is sized for slidable engagement with the tube 130, earlier described, to permit a free longitudinal movement between the tube 130 and inside wall surface 232.

As illustrated with reference to FIGS. 5 and 6, the first arcuate guide portion 222 may be substantially perpendicular to the first arm distal end 216, and the second arcuate guide portion 224 may be substantially perpendicular to the second arm distal end 218. The tube guide 228, therefore, may be generally perpendicular to the arm distal ends 216, 218 when the forceps 200 is in the closed position 226.

Figure 4A:
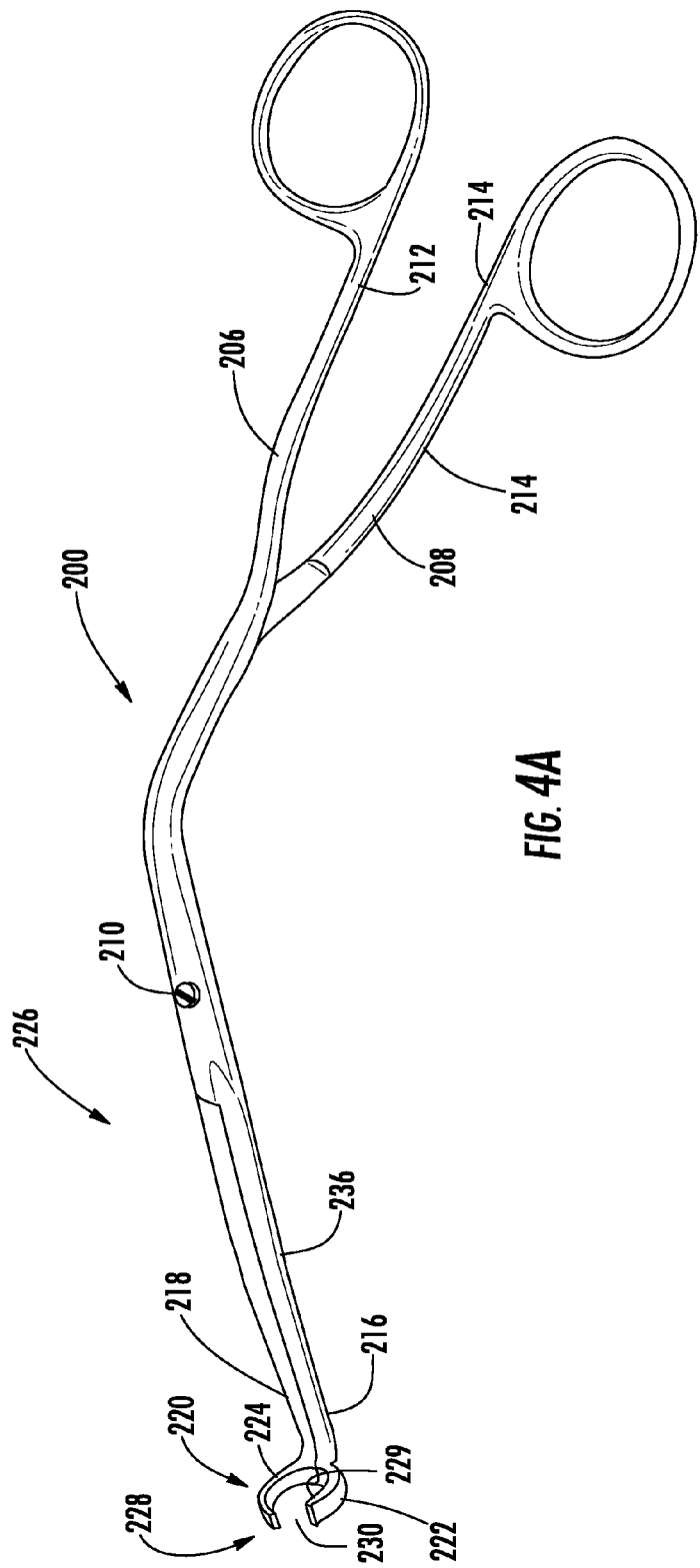
FIG. 4A is a second perspective view of the forceps of FIG. 4.
Figure 4B:
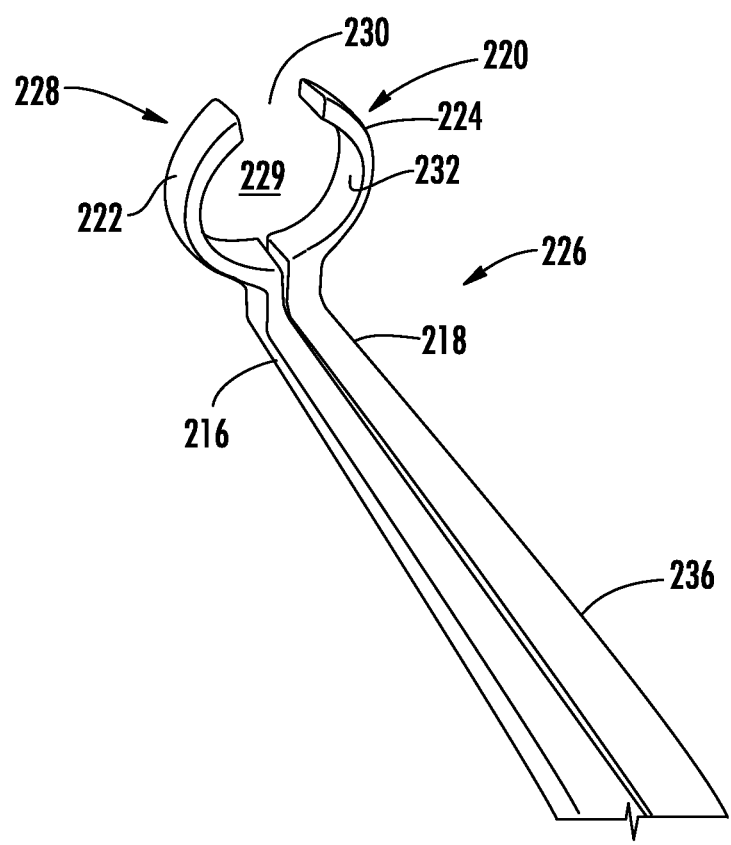
FIG. 4B is a partial perspective view of a distal portion of the forceps of FIG. 4.
Figure 5:
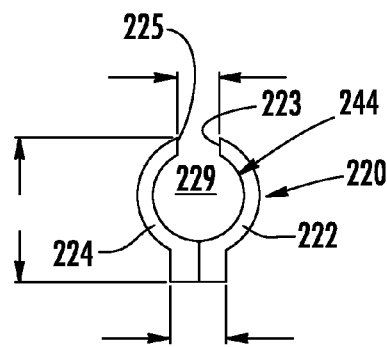
FIGS. 5 and 6 are partial end and side views, respectively, illustrating tip portions of the forceps of FIG. 4.
Figure 6:
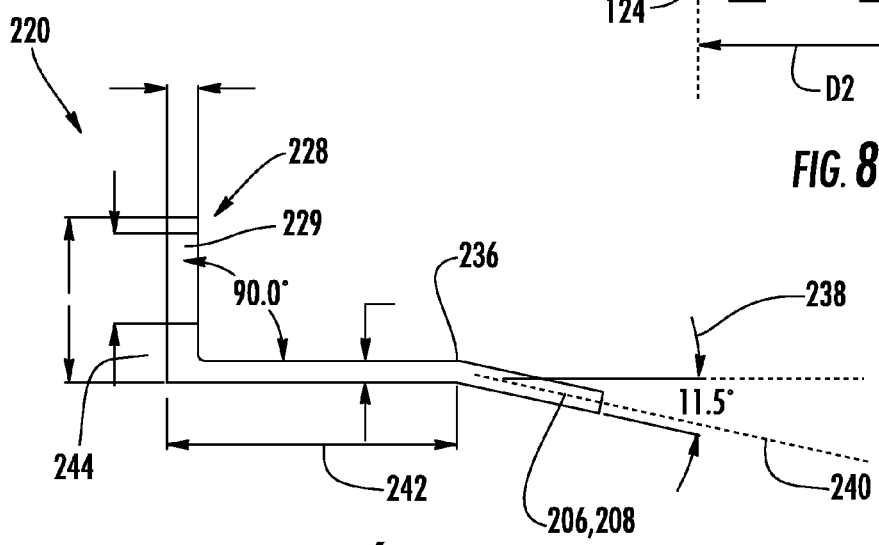

With continued reference to FIGS. 4A and 5, the tube guide 228 includes a gap 230 formed between ends 223, 225 of each of the first and second arcuate guide portions 222, 224, respectively, when the arms 206, 208 are in the closed position 226. It has been shown that a desirable gap dimension is within a range of 12% to 16% of a perimeter measure (i.e. 12% to 16% of the perimeter of a circle) of the opening 229 formed by the inside wall surface 232 of the guide 228.

With reference again to FIGS. 4 and 6, each arm 206, 208 may comprise a bend 236 fixed at the distal ends 216, 218. For the embodiment herein described by way of example, it has also be shown that the bend 236 is preferably fixed at an angle 238 between ten and twelve degrees as measured from an offset of a longitudinal axis 240 of each arm 206, 208. The bend 236 may be positioned at a distance from the guide 228 so as to form a distal arm portion 242 for each arm 206, 208. A length dimension of the distal arm portion 242 may be at least three times a length dimension of a diameter 244 of the opening 239. As earlier described for the known forceps 100 illustrated with reference to FIGS. 1 and 2, it will be appreciated by those of skill in the art now having the benefit of the teachings of the present invention that the forceps 200 may comprise multiple bends as described for the forceps 100 such that the bend 236 may be the fourth bend 142 earlier described and the forceps 200 may include first, second and third bends as described for the forceps 100 without departing from the teachings of the present invention.

The improvements herein described for the forceps 200 including the gap 230 having a dimension of approximately 12% to 16% of the opening's 239 medial circumference provides a desirable solution when compared to previously known forceps having a complete arcuate enclosure, or only a slight gap resulting from the generally non-machined tolerances of typical forceps. The gap 230 is evenly split above and below its original opening point.

The teachings of the present invention contemplate multiple forceps 200, such as those sized for pediatric, adolescent and adult use. A Table illustrating some but not limited desirable dimensions for elements of the embodiments herein presented is shown in FIG. 7. By way of example, the gap 230 may be 3mm, 4.5mm, and 6mm in length between ends 223, 225 for pediatric, adolescent, and adult forceps 200, respectively. The gaps of the three sizes are approximately (more or less) 13% gap for the pediatric, an approximate 15% gap for the adolescent and an approximate 15.9% gap in the adult to a medial aspect (the side where the guide portion 222, 224 are not attached to the arms 206, 208).

Experimentation and testing have shown that the gap 230 as herein presented greatly improves time, safety and efficiency of engagement and disengagement (grabbing and letting go of the tube, by way of example). With such an improvement, the user can manipulate the tube more quickly and more easily than known forceps because the gap size may be only slightly smaller than an outside diameter of the tube size that is used with the sized forceps. Therefore, the forceps 200 does not need to be opened, and thus closed, as much as known forceps, and can complete the same procedure in less space or distance, D1 versus D2 as illustrated with reference to FIG. 8, which is especially desirable in a small or traumatized mouth.

By way of further example and with reference to the Table of FIG. 7, one can grasp and release the typically firm endotracheal tube 130 by closing and opening the forceps 1.3 mm (versus 4.3 mm) for pediatric, 1.8 mm (versus 6.3 mm) for adolescent, and 2.3 mm (versus 8.3 mm) for adult. If the forceps do not need to be opened as wide as is typical in the art, by way of example only 30% versus 100% of endotracheal tube diameter, the forceps 200 will be easier to open and close around the tube 130. Further, if an operator only has to open or close the forceps 200 2.5 mm versus 8.5 mm, in an adult for example, a significant decrease in the movement of the arms 206, 208 (which may be as much as about 200% or as desired) is realized, along with a concomitant reduction in the movement of the operator's hand needed to open the forceps 200, (necessary to open and close the forceps around the diameter of the tube 130). There is clearly a significant space saving benefit and realized value.

Figure 7A:
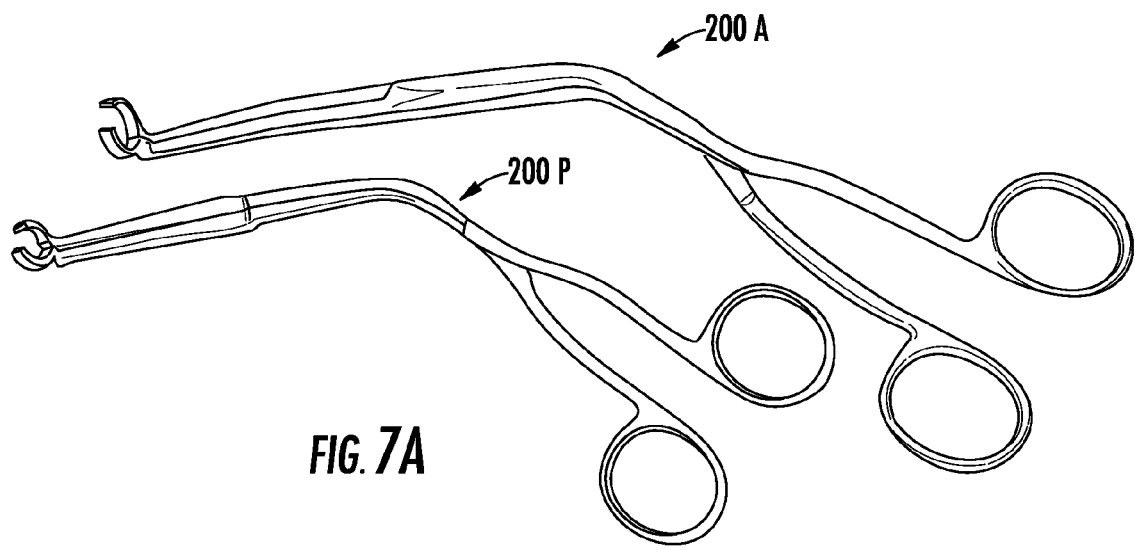
FIGS. 7A and 7B illustrate two forceps and tip portions thereof, respectively, of different size to accommodate adolescent and pediatric patients, by way of example.
Figure 7B:
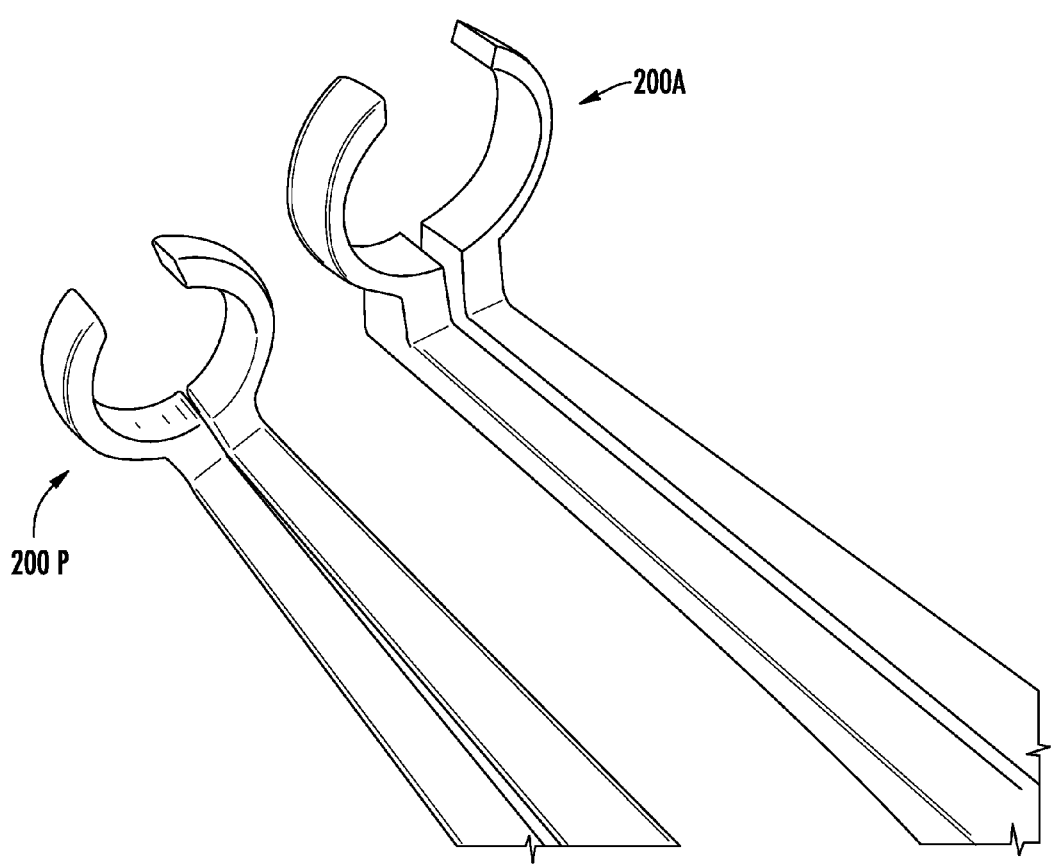

By way of example, reference is made to FIGS. 7A and 7B illustrating manufactured forceps of different sizes, herein illustrated for an adult forceps 200A and a pediatric forceps 200P. As will be appreciated by those skilled in the art, features are similar except for dimensions.

Figure 9:
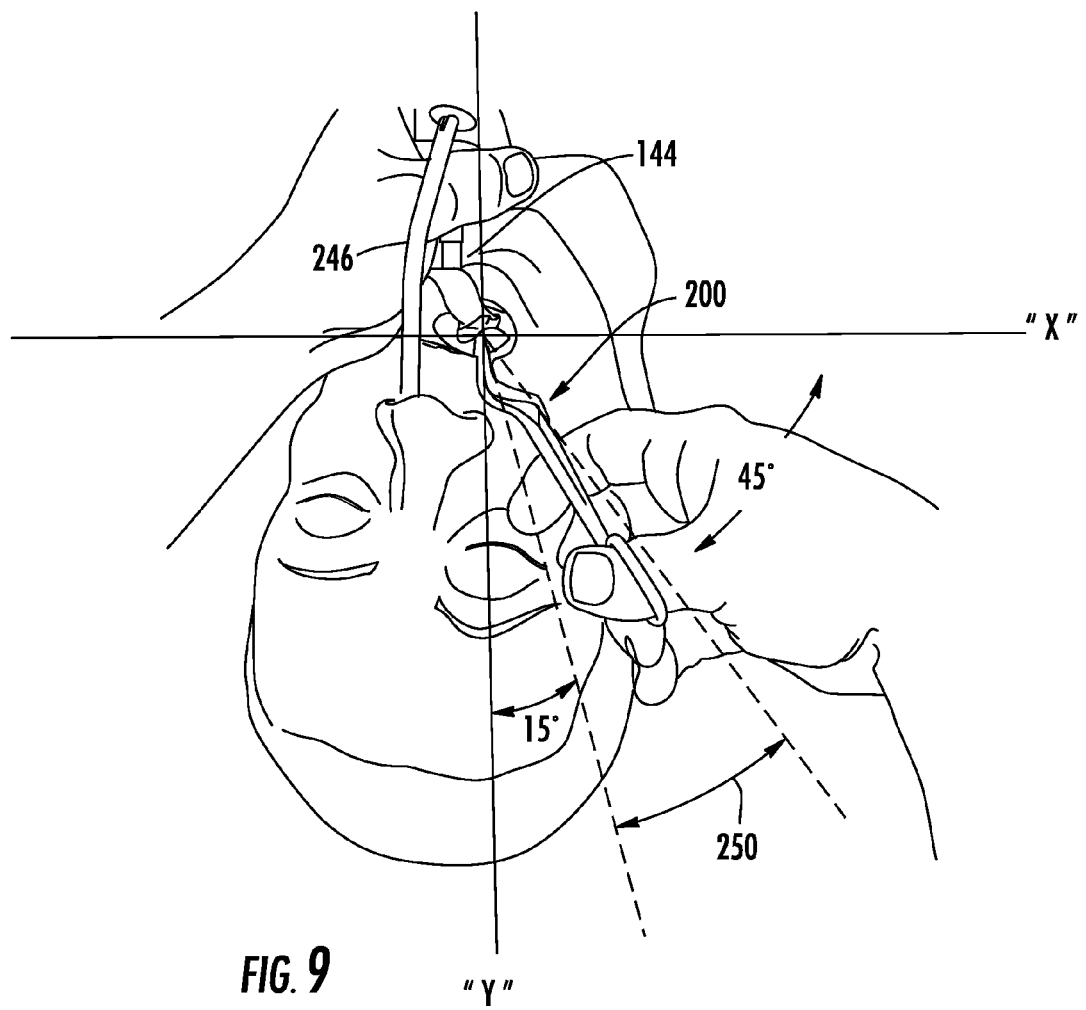
FIG. 9 is a diagrammatical representation illustrating use of one embodiment of the invention in a patient.
Figure 10:
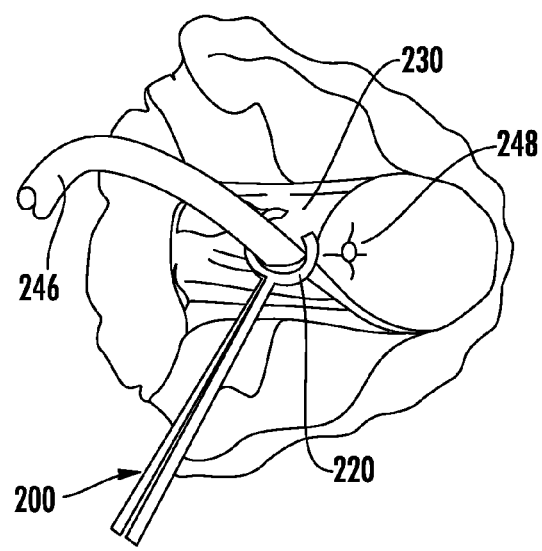
FIG. 10 is a partial enlarged view of a portion of the representation of FIG. 9.

FIGS. 9 and 10 diagrammatically illustrate a nasal endotracheal intubation in a patient using the forceps 200 and laryngoscope 144, wherein a ventilation tube 246 is inserted into the patient's nose and passed through the patient's sinus cavity into the back of the patient's throat. The laryngoscope 144 is used to secure the patient's tongue and provide light to the patient's throat. As the medical professional holds the forceps 200 in registry with the patient's glottis 248, a medical assistant, such as a nurse, will advance the ventilation tube 246 through the tip 220 of the forceps 200 and through the patient's glottis 248. According to the teachings of the present invention and for the illustration herein presented, a desirable orientation of the forceps is within a range 250 between approximately 15 degrees and 45 degrees as measured between "x" and "y" axes, the "y" axis running along the length of the patient's head/body (i.e. along the patient's nose and across the center of the mouth) and across the center of the handle of laryngoscope 144, and the "x" axis being perpendicular thereto. Such an orientation provides an optimum arm position for the physician handling the forceps while simultaneously keeping the physician's hand out of the way of the mouth, permitting an unobstructed view down the patient's throat while permitting the physician optimal range of movement.

Figure 11:
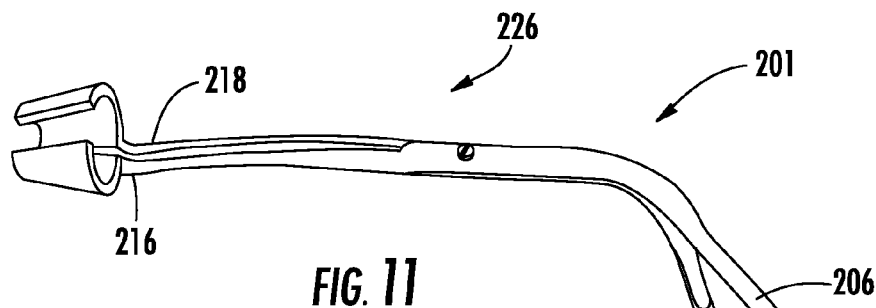
FIG. 11 is a perspective view of an alternate embodiment of forceps in keeping with the teachings of the present invention, wherein a tip of the forceps includes a conical shape.

By way of further example with regard to embodiments of the invention, reference is now made to FIG. 11, wherein an alternative embodiment of the forceps 201 is illustrated. For the embodiment herein described by way of example, each arm 206, 208 has distal ends 216, 218 having a tip portion that is substantially shaped as half of a cone (or, alternatively, as half of a cylinder). When the arms are in the closed position 226, as illustrated in FIG. 11, the ends together form a cone-shaped (or cylindrically-shaped) guide adapted to receive and guide a catheter so that the catheter can be advanced into the patient's glottis. The diameter of the cone-shaped ends, when closed, is preferably slightly larger than 8 mm across at its narrowest point. The portion of the ends that is closer to the handles preferably has a diameter larger than 8 mm. In the closed position, the interior surface of the hollow guide formed by the cone-shaped ends acts as a funnel to allow the medical professional to more easily guide the end of a catheter through the cone-shaped ends. It is understood that the size of the guide formed by the ends may be varied within the scope of this invention depending upon the diameter of the catheter, including but not limited to catheters that are used in pediatric, adolescent and adult patients. As above described for the forceps 200, the forceps 201 includes a tip having a gap therein when the forceps are in the closed position.

Figure 12:
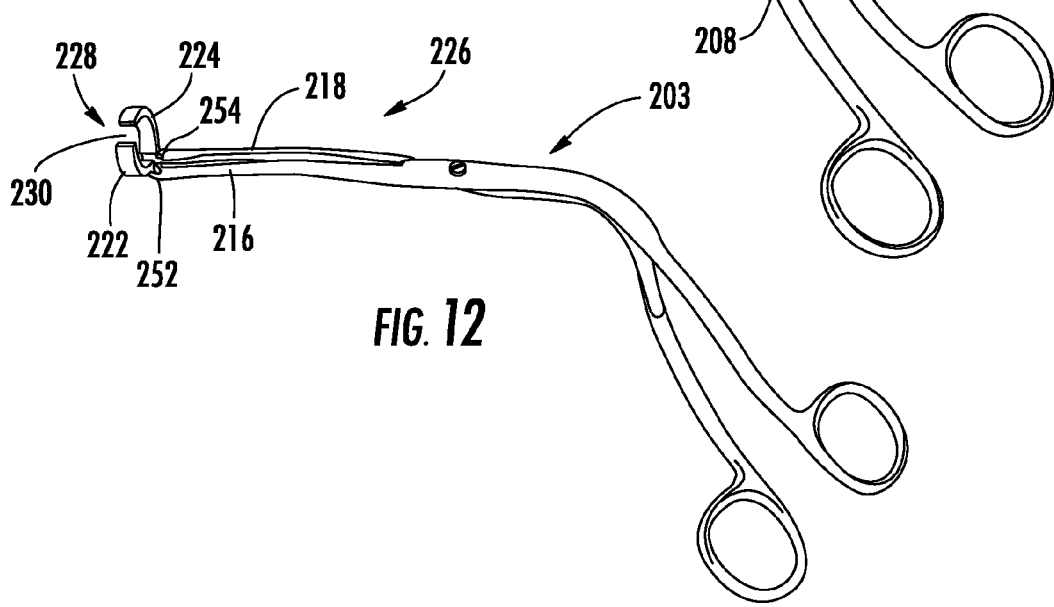
FIG. 12 is a perspective view of an alternate embodiment of forceps in keeping with the teachings of the present invention, wherein a tip of the forceps is hingedly attached to arm portions of the forceps.
Figure 13:
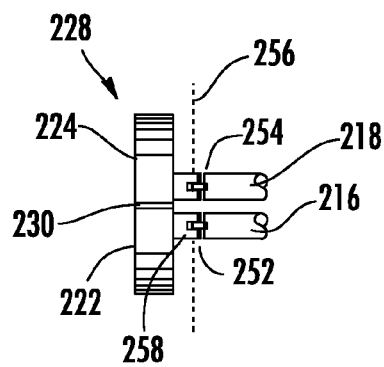
FIG. 13 is a plan view of the tip portion of the forceps of FIG. 12.
Figure 14:
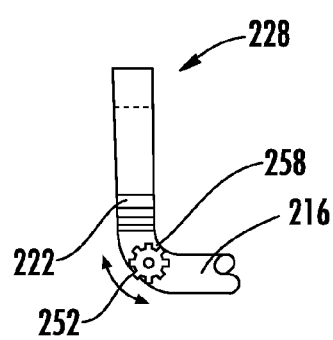
FIG. 14 is a side view of the tip portion of the forceps of FIG. 12.

With reference now to FIGS. 12-14, another alternative embodiment of the forceps 203 is illustrated by way of example. The shape of the ends 222, 224 may, within the scope of the invention, be any shape that would allow the ends to form the guide tube 228 when in the closed position 226, as earlier described, such that a catheter may be easily passed therethrough. For the forceps 203, the ends 222, 224 are pivotally connected to arm distal ends 216, 218, respectively, by joints 252, 254. The joints 252, 254 are preferably located about the same axis 256. The ends 222, 224 are permitted to rotate about the joints 252, 254 to allow for immediate adaptation of the forceps 203 to the angle of insertion required by a patient's body. Any suitable means may be employed for releasably retaining the ends 222, 224 in any desired angular position relative to arm distal ends 216, 218 or arms 206, 208, such as opposed serrations or teeth 258. As a result, the medical professional using the forceps 203 is not required to use a different forceps, but may change the orientation of the ends 222, 224 when discovering that a different angle of insertion of a catheter is required by a particular patient's anatomy. As above described with reference to the forceps 200, the gap 230 is a feature providing desirable benefits.

By way of further example, earlier thinking for forceps designs was to completely encircle the endotracheal tube for maximum control of the tube. Testing and experimentation has shown that similar control of endotracheal tubes can be accomplished if there is a gap or opening in the medial aspect of the circumference of the tip. Having the forceps completely encircle the endotracheal tubes takes more time and effort to grasp and much more time and greater difficultly to release the endotracheal tubes, especially in patients with small mouths relative to the operator's size (height/weight). Without the gap, releasing the endotracheal tube required rotating the instrument so that the opposed surfaces of the gripping portions aligned with the bottom of the endotracheal tube before releasing of the tube. The gap makes that extra and potentially damaging, time consuming and dangerous maneuver unnecessary. Instead of prolonging the procedure, the physician wants to shorten the duration of the procedure.

With control of the tube being equal, the gap, or opening provides a quicker and safer grasping and even quicker and safer, and more efficient, releasing of the endotracheal tube after the endotracheal tube is in place and the procedure of placing the tube is complete.

Benefits, other advantages, and solutions to problems have been described above with regard to specific embodiments of the present invention. However, the benefits, advantages, solutions to problems, and any element(s) that may cause or result in such benefits, advantages, or solutions to become more pronounced are not to be construed as a critical, required, or essential feature or element of any or all the claims. As used herein and in the appended claims, the terms "comprises," "comprising" or any other variation thereof is intended to refer to a non-exclusive inclusion, such that a process, method, apparatus or article of manufacture that includes a list of elements does not include only those elements in the list, but may include other elements not expressly listed or inherent to such process, method, apparatus or article of manufacture.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and alternative embodiments are intended to be included within the scope of the appended claims.

That which is claimed is:

1. An intubating forceps comprising:
   first and second arms pivotally connected by a pivot for relative movement between an opened position and a closed position, each arm having a distal end and a proximal end;
   a first arcuate guide portion at the distal end of the first arm;
   a second arcuate guide portion at the distal end of the second arm;
   a tube guide having an opening therethrough formed by the first and second arcuate guide portions in combination when the arms are in or proximate the closed position;
   the tube guide having an inwardly facing arcuate inside wall surface forming the opening, wherein the opening is sized for slidable engagement with a tube to permit free longitudinal movement therewith;
   wherein the first arcuate guide portion lies in a plane substantially perpendicular to the first arm, and the second arcuate guide portion lies in a plane substantially perpendicular to the second arm, the tube guide thus generally perpendicular to the arms when the arms are in the closed position;
   wherein the tube guide includes a gap formed between tip ends of each of the first and second arcuate guide portions when the arms are in the closed position, the gap dimensioned to be within a range of 12% to 16% of a perimeter measure of the opening formed by the inside wall surface of the guide; and
   wherein each arm comprises a bend fixed at distal ends thereof, the bend fixed at an angle between ten and twelve degrees offset from a longitudinal axis of each arm, wherein the bend is positioned at a distance from the guide that is at least three times a length dimension of a diameter of the opening.

2. The forceps according to claim 1, wherein the bend comprises a fourth bend, and wherein each arm includes a first bend and a second bend located between the pivot and the proximal ends of each arm, the arms along each of the first and second bends being substantially parallel with each other when in a closed position, and each arm further defining a third bend located between the second bend and the proximal end of the arms, the arms along the third bend being substantially parallel with each other when in the closed position, the bends oriented in such a way that the proximal ends of each arm avoid visually interfering with the distal ends when the distal ends of each arm are placed inside a pharynx of a patient, allowing an unobstructed view of vocal cords.

3. The forceps according to claim 2, wherein the first, second and third bends are in an area substantially equidistant between the pivot and the proximal ends of the arms.

4. The forceps according to claim 2, wherein the angle formed by the second bend is substantially 120 degrees, the angle formed by the third bend is substantially 150 degrees.

5. The forceps according to claim 2, wherein the first bend lies about a first axis, the second bend lies about a second axis, the third bend lies about a third axis, and the first, second, and third axes are non-parallel to each other.

6. An intubating forceps comprising:
first and second arms pivotally connected by a pivot for relative movement between an opened position and a closed position, each arm having a distal end and a proximal end;
a tube guide having an opening therethrough formed by first and second arcuate guide portions when the arms are in or proximate the closed position; and
the tube guide including a gap formed between tip ends of each of the first and second arcuate guide portions when the arms are in the closed position, the gap dimensioned to be within a range of 12% to 16% of a perimeter measure of the opening formed by the inside wall surface of the guide.

7. The forceps according to claim 6, wherein the tube guide includes an inwardly facing arcuate inside wall surface forming the opening, and wherein the opening is sized for slidable engagement with a tube to permit free longitudinal movement therewith.

8. The forceps according to claim 6, wherein each arm comprises a bend fixed at distal ends thereof, and wherein the bend is positioned at a distance from the guide that is at least three times a length dimension of a diameter of the opening.

9. The forceps according to claim 6, wherein the first arcuate guide portion lies in a plane substantially perpendicular to the first arm, and the second arcuate guide portion lies in a plane substantially perpendicular to the second arm, the tube guide thus generally perpendicular to the arms when the arms are in the closed position.

10. The forceps according to claim 6, wherein the tube guide is substantially cone shaped.

11. The forceps according to claim 6, wherein the tube guide is rotatably connected to the arms.

12. An intubating forceps comprising:
first and second arms pivotally connected by a pivot for relative movement between an opened position and a closed position, each arm having a distal end and a proximal end;
a first arcuate guide portion at the distal end of the first arm;
a second arcuate guide portion at the distal end of the second arm;
a tube guide having an opening therethrough formed by the first and second arcuate guide portions in combination when the arms are in or proximate the closed position;
wherein each arm comprises a bend fixed at distal ends thereof, the bend fixed at an angle between ten and twelve degrees offset a longitudinal axis of each arm, wherein the bend is positioned at a distance from the guide that is at least three times a length dimension of a diameter of the opening; and
wherein the tube guide includes a gap formed between tip ends of each of the first and second arcuate guide portions when the arms are in the closed position, the gap dimensioned to be within a range of 12% to 16% of a perimeter measure of the opening formed by the inside wall surface of the guide.

13. The forceps according to claim 12, wherein the first arcuate guide portion lies in a plane substantially perpendicular to the first arm, and the second arcuate guide portion lies in a plane substantially perpendicular to the second arm, the tube guide thus generally perpendicular to the arms when the arms are in the closed position.

14. The forceps according to claim 12, wherein the tube guide includes an inwardly facing arcuate inside wall surface forming the opening, wherein the opening is sized for slidable engagement with a tube to permit free longitudinal movement therewith.

15. An intubating system comprising forceps and intubating tube in combination, the system comprising:
a tube having an outside diameter:
a forceps having first and second arms pivotally connected for movement between an opened position and a closed position;
a tube guide having an opening therethrough formed by first and second arcuate guide portions at distal ends, respectively, of the first and second arms when the arms are in or proximate the closed position;
the tube guide having an inwardly facing arcuate inside wall surface forming the opening, wherein the opening is sized for slidable engagement with the tube to permit free longitudinal movement therewith;
wherein the tube guide includes a gap formed between tip ends of each of the first and second arcuate guide portions when the arms are in the closed position, the gap dimensioned to less than the outside diameter of the tube and within a range of approximately 0.25 mm to 1.25 mm; and
wherein the gap is within a range of 12% to 16% of a perimeter measure of the opening formed by the inside wall surface of the tube guide.

16. The system according to claim 15, wherein the first arcuate guide portion lies in a plane substantially perpendicular to the first arm, and the second arcuate guide portion lies in a plane substantially perpendicular to the second arm, the tube guide thus generally perpendicular to the arms when the arms are in the closed position.

17. The system according to claim 15, wherein each arm comprises a bend fixed at distal ends thereof, the bend fixed at an angle between ten and twelve degrees offset a longitudinal axis of each arm, wherein the bend is positioned at a distance from the guide to form a distal arm portion for each arm, and wherein a length dimension of the distal arm portion is at least three times a length dimension of a diameter of the opening.

18. The forceps according to claim 17, wherein the bend comprises a fourth bend, and wherein each arm includes a first bend and a second bend located between the pivot and the proximal ends of each arm, the arms along each of the first and second bends being substantially parallel with each other when in a closed position, and each arm further including a third bend located between the second bend and the arm proximal end, the arms along the third bend being substantially parallel with each other when in the closed position, the bends oriented in such a way that the proximal ends of each arm avoid visually interfering with the distal ends when the distal ends of each arm are placed inside a pharynx of a patient, allowing an unobstructed view of vocal cords.

* * * * *